(12) United States Patent
Dogaru et al.

(10) Patent No.: US 6,504,363 B1
(45) Date of Patent: Jan. 7, 2003

(54) SENSOR FOR EDDY CURRENT TESTING AND METHOD OF USE THEREOF

(76) Inventors: Teodor Dogaru, Center for Precision Metrology, UNC Charlotte, Charlotte, NC (US) 28223; Stuart T. Smith, 1500 Princeton Ave., Charlotte, NC (US) 28209

( * ) Notice: Subject to any disclaimer, the term of this patent is extended or adjusted under 35 U.S.C. 154(b) by 0 days.

(21) Appl. No.: 09/521,540

(22) Filed: Mar. 7, 2000

(51) Int. Cl.[7] .................. G01N 27/82; G01R 33/09
(52) U.S. Cl. ..................... 324/235; 324/238
(58) Field of Search ................. 324/235, 238, 324/240, 242, 252; 338/32 R

(56) References Cited

U.S. PATENT DOCUMENTS 6,150,809 A    11/2000  Tiernan et al.

OTHER PUBLICATIONS

E.S. Boltz and T.C. Tiernan, "New Electromagnetic Sensors for Detection of Subsurface Cracking and Corrosion," Rev. Progress in Quantitative Nondestructive Evaluation, pp. 1033–1038, 1998.

E.S. Boltz, D.W. Cutler and T.C. Tiernan, Low–Frequency Magnetoresistive Eddy–Current Sensors for NDE of Aging Aircraft, SPIE 3397: 39–49, 1998.

E.S. Boltz, S.G. Albanna, A.R. Stallings, Y.H. Spooner, J.P. Abeyta, "Giant Magnetoresistance Imaging for NDE of Conductive Materials," Mat. Res. Soc. Symp. Proc., pp. 151–156, 2000.

*Primary Examiner*—Walter E. Snow
(74) *Attorney, Agent, or Firm*—Lynn E. Barber

(57) ABSTRACT

A giant magnetoresistive (GMR) based eddy current sensor including a giant magnetoresistive sensor integrated on a silicon chip with a signal conditioning circuit and a circular coil.

19 Claims, 22 Drawing Sheets

SENSOR FOR EDDY CURRENT TESTING AND METHOD OF USE THEREOF

BACKGROUND OF THE INVENTION

1. Field of the Invention

This invention relates to a sensor for eddy current testing for locating of surface or near-surface flaws in electrically conductive materials.

2. Description of the Related Art

Use of eddy currents in nondestructive testing of specimens has been known from late in the $19^{th}$ century. Increased research on nondestructive testing has been motivated by the need for precise evaluation of cracks and flaws for the assessment of the expected life of mechanical components. Methods for such testing for detection of defects such as fatigue cracks, inclusions, voids, and the like include dye penetrants, x-ray and ultrasonic testing, and eddy current testing (ECT) in conductive materials.

Many different methods are known for eddy current testing to locate surface or near-surface flaws in electrically conductive materials. Generally, the methods are based on inducing small circular electrical currents (eddy currents) in metallic materials using a coil excited by an alternating current. When appropriately arranged, the excitation magnetic field in the near surface region is perpendicular to the surface, thereby inducing circular currents in the plane of the surface. The disruption of the eddy currents by a discontinuity is similar to the disruption of magnetic fields, except that a wider variety of discontinuities and physical properties affect eddy currents, such as changes in grain size; surface treatment (especially heat treatment); coating thickness; hardness; integrity caused by discontinuities such as cracks, inclusions, dents and holes; dimensions such as thickness, eccentricity, diameter, or separation distance; and alloy composition.

A typical eddy current technique that is known in the art utilizes a coil placed close to the area to be inspected to which an alternating current of 50–500,000 Hz is applied. Changes in the specimen that affect the generation of eddy currents are detected as a change in the impedance (Z, the ratio of coil voltage to coil current) of the coil and are sensed through phase changes in the voltages or currents in the exciting or sensing coils. This change in the impedance may be seen in the deflection of a meter, an oscilloscope presentation, a strip chart recording, lights or alarm actuation, digital readouts or operation of a manufacturing process.

Eddy current testing as now known utilizes any of a large variety of coil configurations depending on one or more of the following: the electrical characteristics and constituents of the component being investigated, the method of detection, the defect information that is desired, and the geometry of the part to be inspected. The field of the current in the specimen being investigated is set up so that it opposes the field producing the current. Two coils may be used in which one coil is used to induce the eddy currents in the specimen (the primary coil), and the second coil is used to sense the eddy current field (secondary coil). Often the sensing coil is smaller, closer to the specimen, and oriented differently than the exciting coil. If the two coils are wound so that their fields oppose each other, the resulting differential coil allows absolute measurement such as single impedance measurement of the two windings as a single coil. A signal is produced only when the specimen near one winding is different from the specimen near the other coil. Such configurations are generally not usable for thickness measurements or for gradual changes in the specimen, but localized corrosion pits and small cracks are well-defined by differential coils.

Alternatively, the magnetic field and its perturbation by discontinuities in the specimen can be detected by Hall effect transducers in place of a secondary coil. One Hall effect transducer can provide a very localized sensing element or an array of sensing elements can be used for examination of small or discrete areas of a specimen.

Many of the prior methods for sensing eddy currents are complicated, are not sufficiently accurate, have insufficient spatial resolution, are bulky, are not sensitive to low fields, are not self-rectifying or directional, or have other limitations. Generally, prior methods of detection of eddy currents use detection in a perpendicular direction to the surface being analyzed. Tangential detection is reported in U.S. Pat. No. 5,864,229, where the detection coils are oriented in parallel direction to the surface (referred to as "current perturbation coils"), and are bulky and do not allow a very localized detection of the field. Also, the probes using these coils cannot be miniaturized or planar integrated on silicon.

Patents for prior eddy current probe testing systems include U.S. Pat. Nos. 5,019,777; 5,068,608; 5,483,160; and 5,864,229. The disclosure of these patents and all other patents referred to herein is incorporated herein by reference.

The invention herein is based on the giant magnetoresistive phenomenon, a recently discovered effect found in metallic thin films consisting of magnetic layers separated by thin nonmagnetic layers a few nanometers thick. Researchers observed a large decrease in the resistance by applying a magnetic field to the films. The cause of this effect is the spin dependence of electron scattering and the spin polarization of conduction electrons in ferromagnetic metals. The effect depends on the relative orientation of the magnetization in the adjacent ferromagnetic layers. If the orientation is parallel, there is minimum electrical resistance of the structure and when the orientation is antiparallel, there is maximum electrical resistance of the structure. When no external field is applied, the adjacent ferromagnetic layers have antiparallel orientation, due to antiferromagnetic coupling of these layers when separated by a nonmagnetic layer (usually copper) of a defined thickness. The initial orientation of the magnetization in the ferromagnetic layers is obtained by either depositing the ferromagnetic layers under the influence of a magnetic fields, which gives the orientation of the magnetization, or by depositing narrow strips of giant magnetoresistive (GMR) films that automatically orient the magnetization (magnetic domains) along the main dimension of the strips, due to the shape-induced anisotropy. When an external field is applied within the plane of the films, the magnetization of all the ferromagnetic layers tends to orient along the direction of this applied field, resulting in the parallel configuration described above, and consequently, in a lower resistance of the structure.

GMR devices (U.S. Pat. Nos. 5,595,830; 5,569,544; and 5,617,071 of Daughton) are used as magnetic field sensors and have been used for measuring displacement, angular position/speed measurement, current measurement, magnetic media detection, magnetic memory, earth's field detection and for biosensors. Although others have used a GMR sensor to detect the vertical (perpendicular to the specimen surface) component of the magnetic field to detect deep buried flaws in aluminum multilayered structures, others have not previously used a GMR sensor to detect fields in a direction parallel to the specimen surface (see Wincheski et al., Review of Progress in QNDE 18: 1177, 1999 and Ward et al., Review of Progress in QNDE 17: 291–298, 1998).

The sensor of the invention herein can be placed closer to the surface of the specimen to be tested than previous sensors, and therefore the device has a higher sensitivity by reducing sensor lift-off. The coil diameter of the invention is greatly reduced in size, which is not physically possible with the previous vertical sensors, and therefore the invention has much better spatial resolution using flat coils on top of the sensor. The integration of the coil and sensor in the invention using planar technology is thus possible in the invention while not being possible in the vertical sensors. With the invention, detection of cracks near edges is possible by eliminating the large signal produced by the edge, using a proper orientation of the sensor's axis, parallel to the edge, which is not possible in the vertical sensor.

It is therefore an object of the invention to provide a simple, small, sensitive uni-polar eddy current sensor that is able to accurately detect axial and circumferential flaws in conductive materials, provide information on cracks, and enhance the spatial resolution of eddy current testing and detect cracks located near the sharp edges.

It is a further object of the invention to provide an eddy current sensor with a simplified signal conditioning circuit that does not require synchronous detection, due to its being a uni-polar device.

It is a further object of the invention to provide an eddy current sensor that has directional characteristics due to the magnetic easy-axis produced by poling the films during deposition.

It is a further object of the invention to provide an eddy current sensor which is used to detect fields coplanar to the specimen surface and in a specific direction within this plane. The flat coils of this sensor can be placed closer to the specimen surface and is very sensitive.

Other objects and advantages will be more fully apparent from the following disclosure and appended claims.

SUMMARY OF THE INVENTION

The invention herein is a giant magnetoresistive (GMR) sensor combined with a circular coil to create an eddy current probe, which is extremely sensitive and able to detect magnetic fields of the order of $10^{-5}$ T. The sensitive axis of the GMR sensor is oriented parallel to the specimen surface.

Other objects and features of the inventions will be more fully apparent from the following disclosure and appended claims.

DETAILED DESCRIPTION OF THE INVENTION AND PREFERRED EMBODIMENTS THEREOF

Figure 1A:
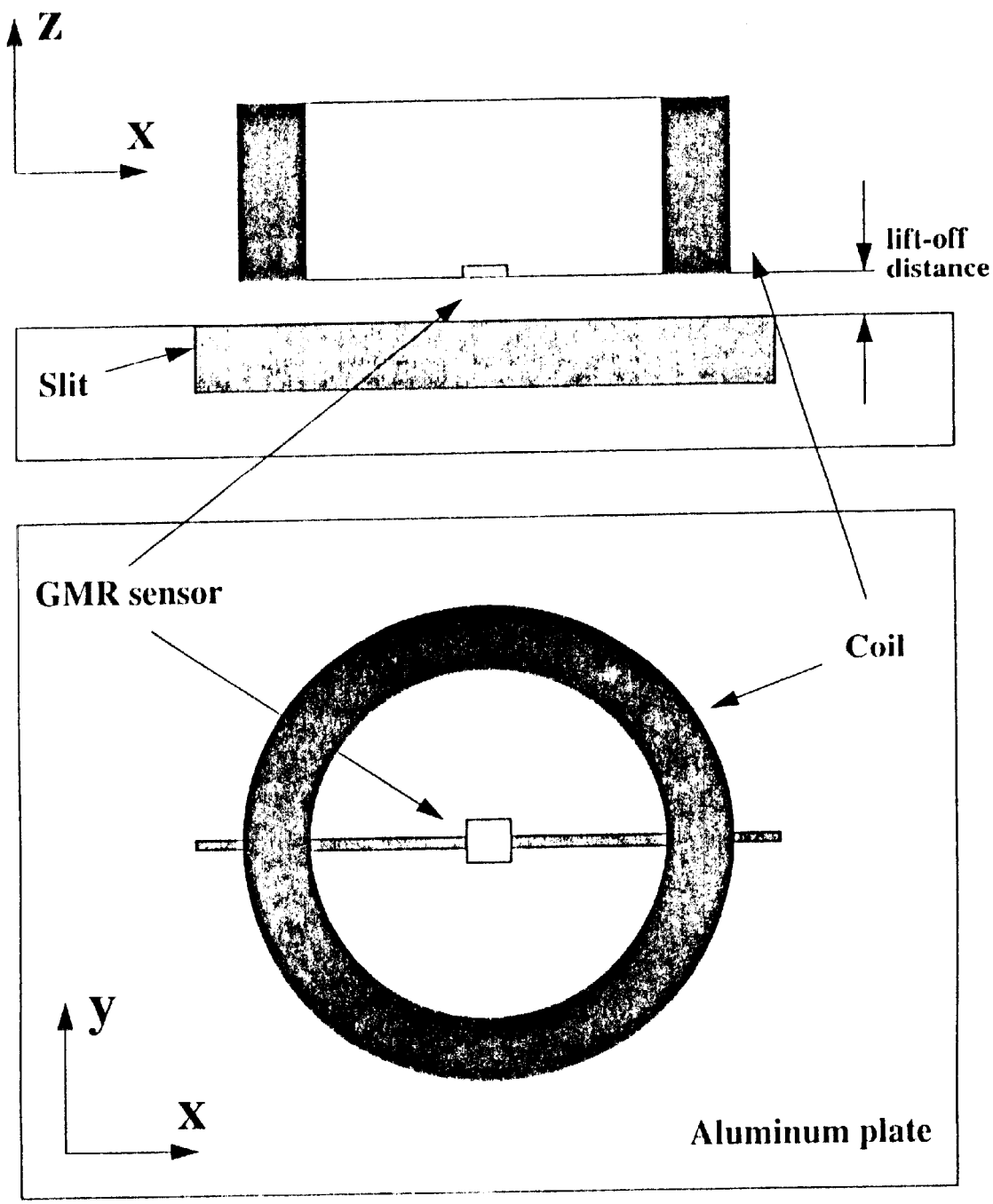
FIG. 1(a) is a schematic diagram indicating how the probe and coordinate system are assembled.

The present invention herein is a giant magnetoresistive (GMR) based eddy current sensor. GMR based eddy current probes according to the invention herein are able to accurately detect flaws in conductive materials. Crack reconstruction is also possible by using results obtained with the GMR based eddy current probe of the invention. The uni-polarity of the GMR sensor leads to a simplified signal conditioning circuit. The tiny dimensions of the sensors of the invention, and the extremely high sensitivity (260 mV $mT^{-1}$) to low magnetic field over a broad frequency range (up to 1 MHz) of the GMR based eddy current sensor enhance its spatial resolution.

In particular, the use of the GMR sensor of the invention provides an attractive alternative for ECT sensing for crack detection. The high sensitivity to low fields makes this kind of sensor suitable for the measurement of relatively small field perturbations due to the presence of the crack. Other characteristics of the GMR sensor that make it unique among the existing transducers used in ECT are its self-rectifying and directional properties. Being uni-polar (i.e., positive output for both positive and negative applied fields), GMR sensors simplify the signal conditioning circuit of the ECT transducer by eliminating the need for synchronous detection. In the presence of fields lower than the saturation value, the resistance of the film will vary almost linearly with the magnitude of the applied field. Upon removal of the applied field, the film resistance returns to the original value with relatively low hysteresis. Fields applied perpendicular to the sensitive axis have little effect on the film.

Additional properties of the invention include:

1) the linearity of the response and the low noise lead to improved performance in terms of the signal to noise ratio;
2) the device is directional, and responds only to the component of the magnetic field along its sensitive axis (hard-axis), enabling relatively high excitation fields (considerably higher than the saturation field of the sensor) in a perpendicular direction without affecting the sensor's output range;
3) directionality enables vector mapping of the magnetic field and thus enhances the possibility of unambiguous crack geometry de-convolution;
4) reduced signal conditioning electronics means a lower cost;
5) being based on thin film, planar technology, microelectronic manufacture and fabrication techniques can be readily applied;
6) the sensitivity is extremely high (260 mV mT$^{-1}$) at very low fields (0.1 Gauss=10$^{-5}$ T), and the characteristic of the sensor (sensitivity and saturation field) can be customized by choosing a proper structure of the GMR multi-layer; and
7) directionality enables detection of cracks near sharp edges. By orienting the sensing axis parallel to the edge, the probe is insensitive to the presence of the edge.

The dimensions of the GMR sensor of the invention, which consists of multi-layers of ultra-thin magnetic and nonmagnetic films, are usually in the range of tens to thousands of micrometers. Consequently, a similar spatial resolution is possible, thus being limited only by the dimensions of the exciting coil (maximum crack length that can be detected is roughly equal to the coil radius).

Generally the eddy current sensor of the invention, comprises:

a) a giant magnetoresistive sensor having a sensing plane and a sensing direction within the sensing plane; and
b) a rotationally symmetric coil having an axis of symmetry, wherein the giant magnetoresistive sensor is centered at the axis of symmetry of the coil, with the sensing plane and sensing direction perpendicular to the axis of symmetry of the coil.

In one preferred embodiment, the coil is a pancake type coil is placed between the giant magnetoresistive sensor and a specimen, parallel to the sensing plane and the sensing direction of the giant magnetoresistive sensor. In the preferred embodiment, the pancake type coil and the giant magnetoresistive sensor are deposited on the same substrate, such as silicon. The substrate material that is used must not accumulate its own eddy currents in a manner that interferes with the use of the invention, nor must it overheat during use. It also must be a flat surface for placement of the planar film of the giant magnetoresistive sensor. In order that the single piece of wire which forms the coil has both of its ends exiting from the exterior of the coil, the number of layers of wire in the coil is preferably a multiple of 2. The coil may be cylindrical with two ends. In this case, the giant magnetoresistive sensor is preferably placed at the end of the cylindrical coil that is closest to a specimen to be measured, with the cylindrical coil surrounding the sensor at that end of the coil. In order to allow measurements, the eddy current sensor further preferably comprises a signal conditioning circuit comprising a differential amplifier and a low pass filter. Most preferably, the sensor has a broad bandwidth enabling a large range of excitation frequencies, in turn enabling variation of skin depth on the surface for measurement of defects of varying depth or of sub-surface defects, and produced in a configuration so that the component of the magnetic field in the direction of the sensitive plane, parallel to the surface of the specimen, can be measured.

The method of use of the eddy current sensor of the invention comprises orienting the sensitive plane of the giant magnetoresistive sensor parallel to the specimen surface; passing an alternating current through the coil placed adjacent to the specimen surface, with the coil placed perpendicular to the surface, to induce a circulating current in the surface plane; setting parameters for scanning the surface; utilizing the sensor to scan the surface to produce an output signal; amplifying and low pass filtering the output signal; collecting data from the amplified and filtered output signal; and plotting three-dimensional maps representing amplified and filtered output signal. The location and length of a detected crack are determined by orienting the sensitive axis of the probe perpendicular to the crack. Further, the sensor is oriented so that the output signal is insensitive to edges of the specimen, but so that perturbations of eddy currents by cracks at the edges are monitored by the probe, which means that in this case the sensing direction is oriented parallel to the specimen edge.

In the GMR sensors tested in the experiments reported herein, the magnetoresistors have serpentine shape, in which there are long narrow strips having a width of 2 $\mu$ and a length of about 100 $\mu$, with a thickness less than 10 nm. The strips are interconnected by perpendicular short strips of the same material. The orientation of the strips gives the sensitive axis, along which the applied field can be sensed. A field applied in a direction perpendicular to the axis cannot rotate the magnetization along that direction, because the magnetic domains have a minimum length, which is typically greater than 2 $\mu$. Therefore, a directional sensor is obtained. The GMR sensors used to obtain the results reported herein are manufactured by Nonvolatile Electronics Company (NVE, AA Series, Eden Prairie, Minn.). The GMR multilayers comprise four to six composite magnetic layers composed of two 10–15 Angstrom CoFe layers at the nonmagnetic interfaces and a single 20–40 Angstrom CoNiFe layer between them, and used 15–18 layers of copper alloys as the nonmagnetic interface layers.

To use the invention, eddy currents are induced, as in the prior art, as a result of the application of an alternating magnetic field to the specimen. Usually this field is produced by passing an alternating current through a coil placed at, or near to, the surface of the specimen (termed "adjacent" herein). When appropriately arranged, the magnetic field in the near surface region is perpendicular to the surface of the specimen thereby inducing circulating currents in the plane of the surface. In the presence of defects, which act as a high resistance barrier, the eddy current flow is perturbed. As a result of this defect, a "leakage" magnetic field is produced.

Such field perturbations are usually detected as an impedance change of the exciting coil. To enhance the sensitivity and spatial resolution of the measurement, more advanced techniques are used that are based on the separation of the excitation and detection elements.

Figure 17:
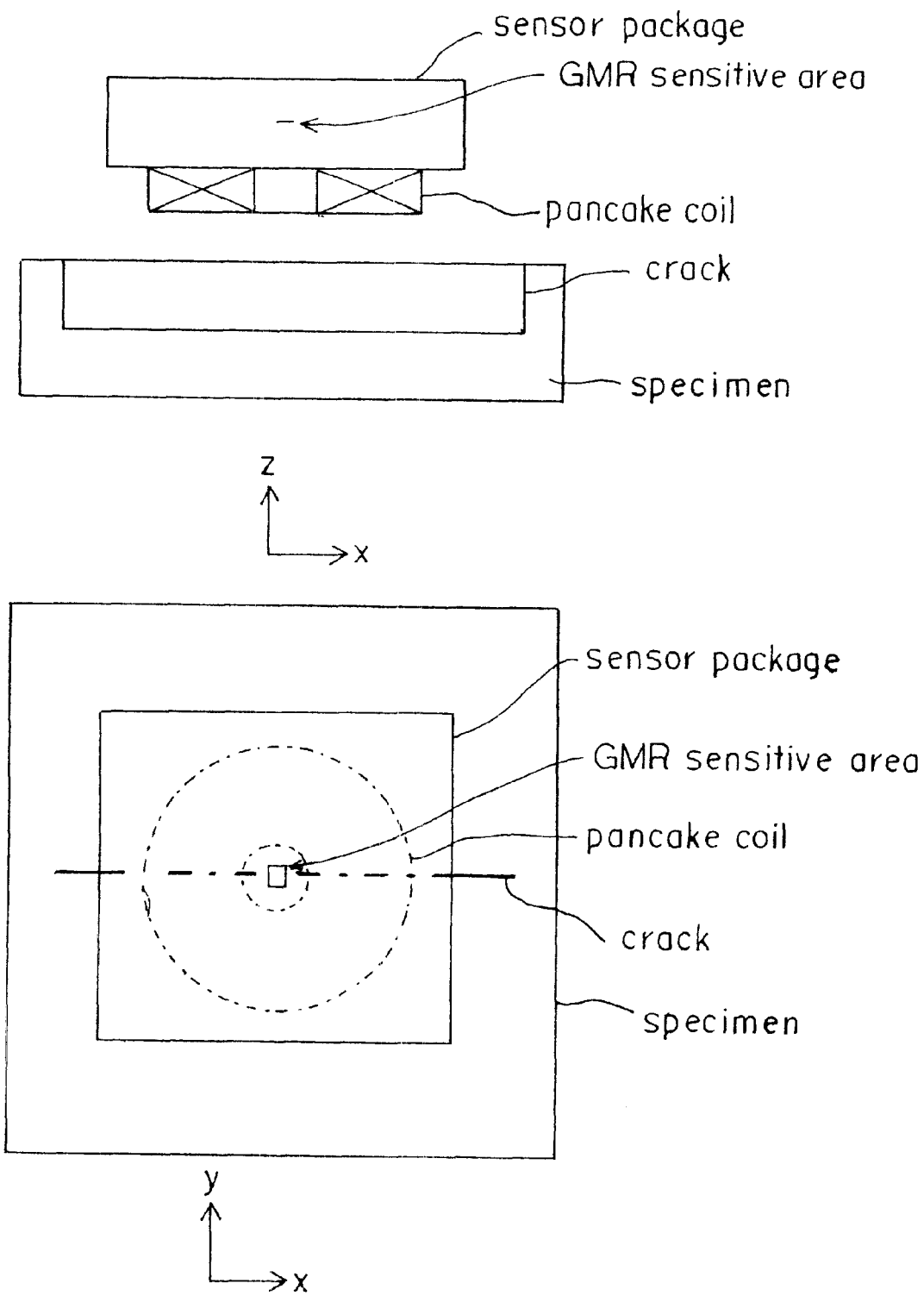
FIG. 17 shows the flat coil placed between the sensor and specimen.

The main components of the eddy current probe of the invention comprise a pancake-type coil, assembled as shown in FIG. 1(a) and a GMR sensor in a Wheatstone bridge configuration. FIG. 1(a) shows the coil geometry. Dimensions of the coil used in experiments which were performed to evaluate the sensor of the invention are: inside radius, 5 mm; outside radius, 5.6 mm; length of coil, 3 mm; number of turns, 33; and diameter of wire, 0.2 mm. The coil is cylindrical, with the axis perpendicular to the specimen surface. The coil completely surrounds the GMR sensor package. To increase the spatial resolution of the crack detection, a flat pancake type coil can be substituted for the cylindrical coil surrounding the sensor package. In the subsequent experiments, the flat coil is placed symmetrically on top of the sensor, between the sensor and the specimen. (FIG. 17) The flat coil used is composed of two winding layers, has 20 turns, an internal radius of 0.8 mm, an external radius of 2.8 mm, a mean radius of 1.8 mm, a thickness of 0.4 mm and a wire diameter of 0.2 mm. Although cylindrical coils have been used before, flat excitation coils are not known in the art. Other rotationally symmetric coils (or at least having one or more pairs of points which are equidistant from the center of the coil at opposite sides of the coil), such as a square or octagonal shape, could be used to create an eddy current probe. The sensor is centered at the axis of symmetry of the coil with its sensing direction, and therefore the plane of the sensor film, perpendicular to this axis.

The sensing element can be produced on a silicon substrate, which can be housed in a standard in-line package and placed at the end of the coil on its symmetry axis as shown in FIG. 1(a).

Experimental evaluation of the probe of the invention is performed by scanning the sensor over the surface of an aluminum plate containing slots of known dimensions. The sensitive axis of the GMR probe is coplanar with the surface of the specimen. As the excitation field produced by the coil is perpendicular to the specimen's surface, in the absence of defects, there is no effect on the sensor. In this way, the detected field, which is the result of the perturbation of the eddy current flow paths due the crack, is separated from the excitation field.

Figure 1B:
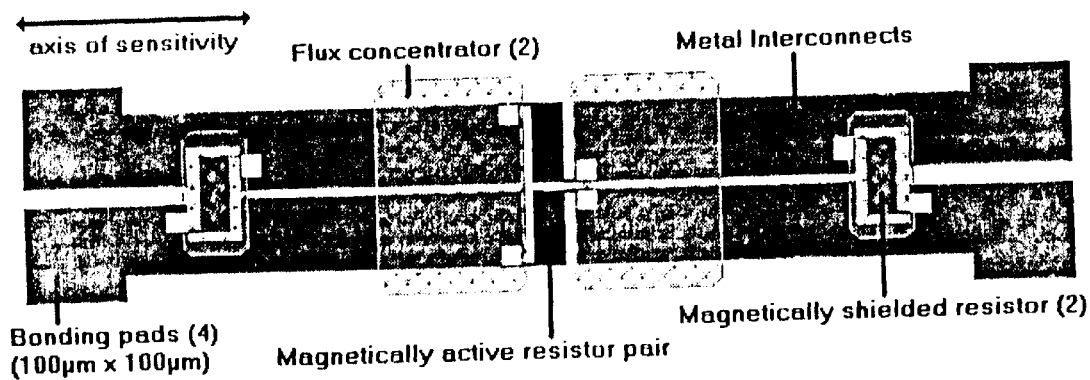
FIG. 1(b) is a schematic diagram of the layout of the sensor of the invention.

A schematic diagram of the sensor of the invention is shown in FIG. 1(b). Each of the components shown in this FIG. can be obtained from NVE (Eden Prairie, Minn.). The role of each of the components is described in U.S. Pat. No. 5,617,071, the disclosure of which is incorporated herein by reference.

The output of the sensor, which is a high frequency rectified signal, is low pass filtered, for example using a preamplifier such as the Low Noise Preamplifier (Stanford Research Systems SR560, Sunnyvale, Calif.), which is used both for preamplifying and for low pass filtering. This instrument is versatile because the amplification and cut-off frequency of the filter can be varied over a large range of values (amplification from 1–100, cut-off frequency from 1 Hz to 1 MHz). After preamplification, the DC component of the signal, being proportional to the amplitude of the field created by the flaw, is immediately extracted.

Figure 2:
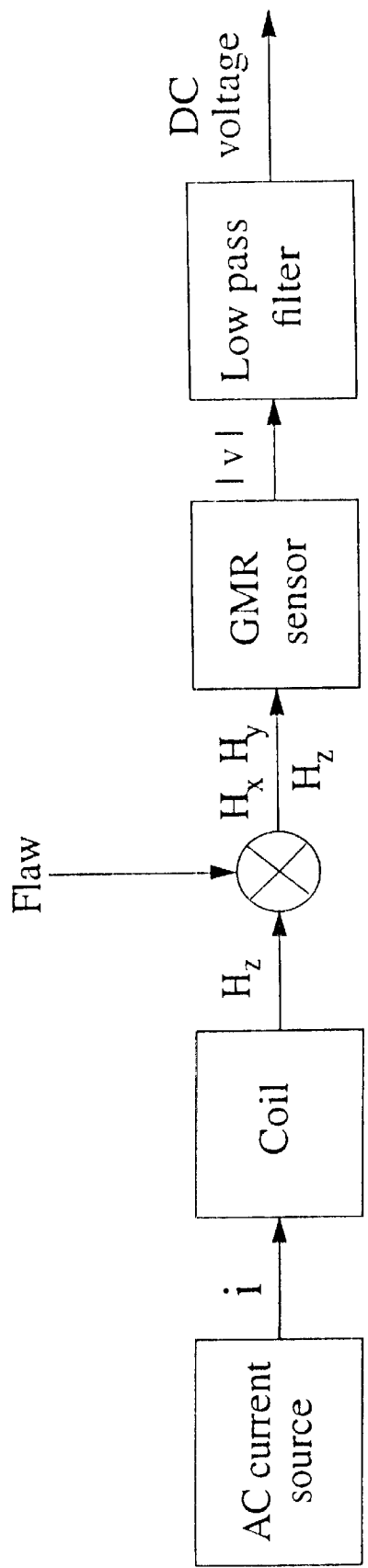
FIG. 2 is a block diagram showing the key components of a preferred embodiment of the probe of the invention.
Figure 3:
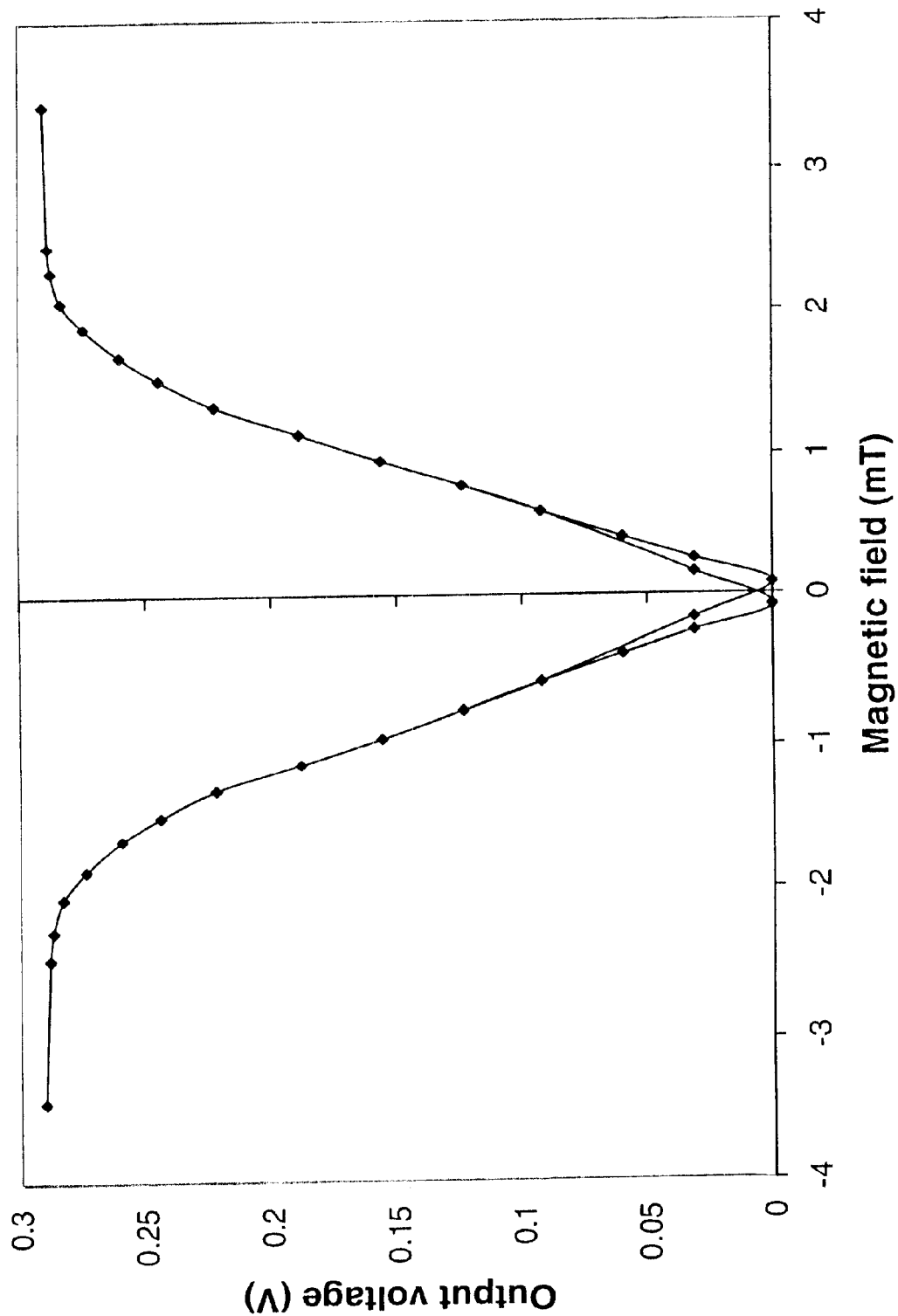
FIG. 3 is a graph of output voltage (V) vs. magnetic field (mT) of the sensor.
Figure 4:
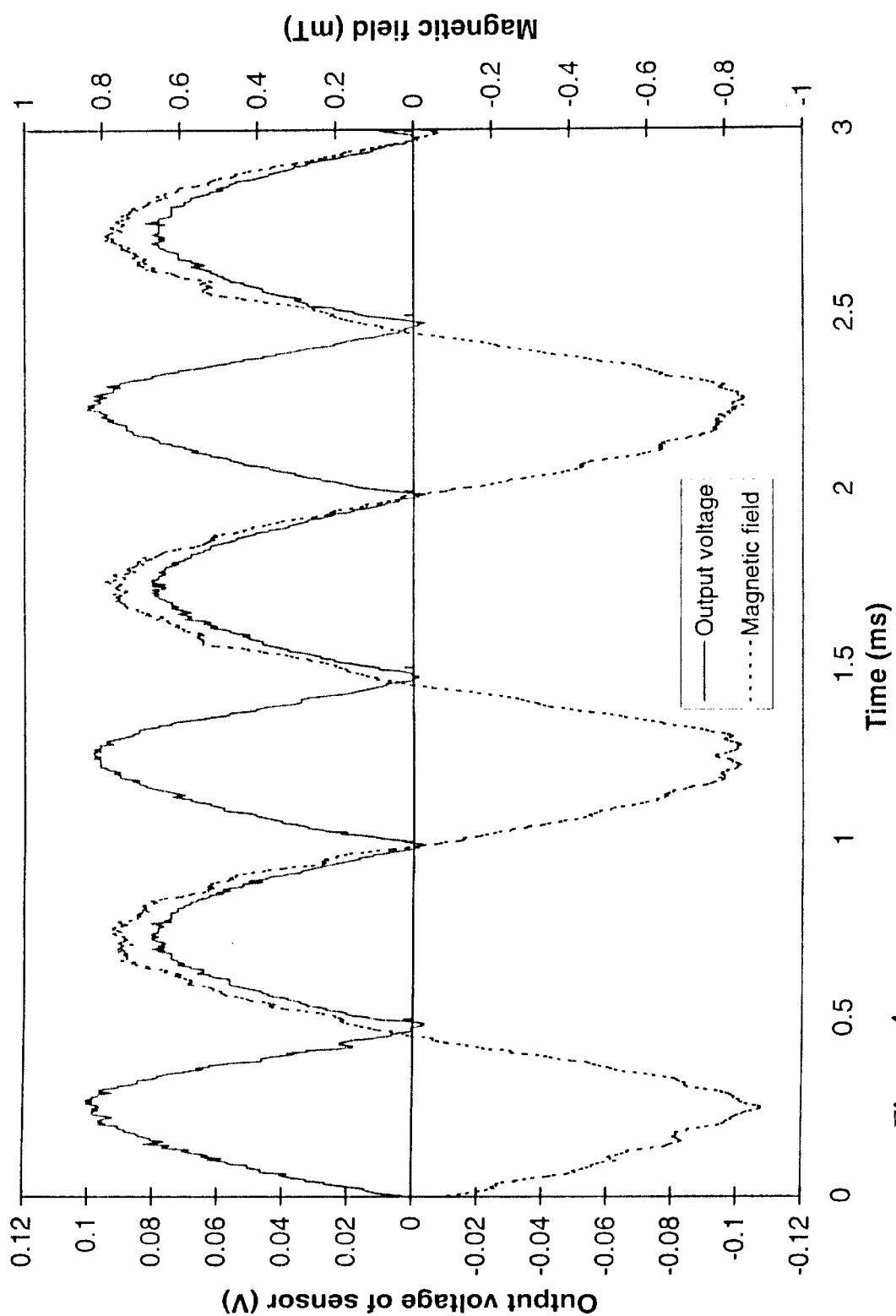
FIG. 4 is a time domain response of the sensor to a sinusoidal applied field of 1 kHz frequency in the direction of sensitive-axis.

A preferred embodiment of the invention is shown in FIG. 2, using a GMR sensor such as Model AA003 (NVE). Only two elements forming opposing arms of the bridge are sensitive, the other two, being magnetically shielded, act only as balancing resistors. The die size of the sensor, which is deposited on a silicon substrate, is 0.44 by 3.37 mm, although the dimensions of the active area of the bridge (the two sensitive resistors) is about 100 by 200 $\mu$m in the middle of the layout. A typical magnetoresistance characteristic of this kind of sensor is shown in FIG. 3 from which the symmetric unipolar action is apparent. The time domain response of the sensor to a sinusoidal applied field of 1 kHz frequency in the direction of sensitive-axis demonstrates the self-rectifying property of the sensor as shown in FIG. 4.

Figure 5:
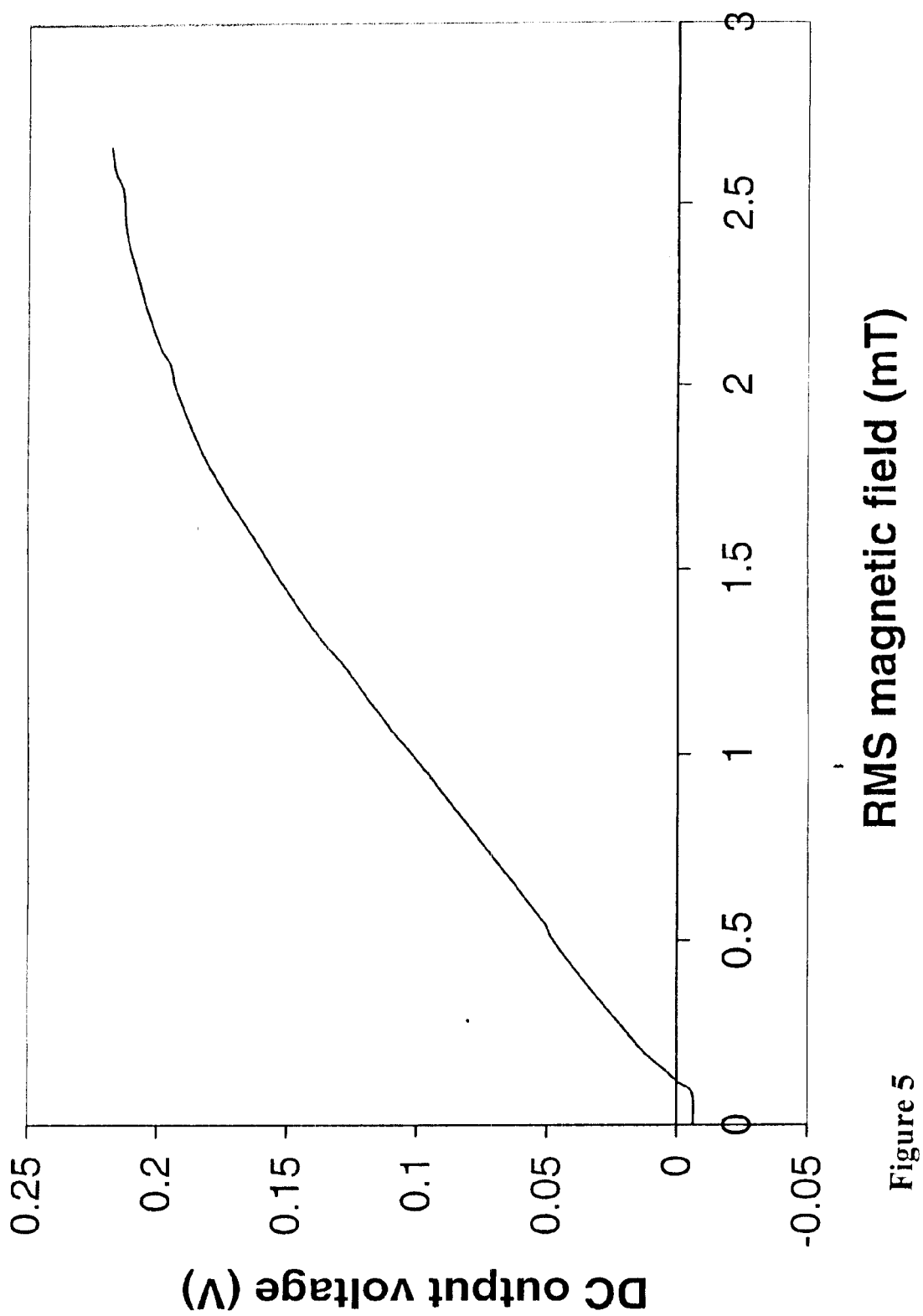
FIG. 5 is a graph showing the AC characteristics of the sensor at 50 kHz.

The invention herein utilizes a prior GMR sensor that is commercially available from NVE, integrated together with the other invention components discussed above, to produce the probe design that forms the heart of the invention. In particular, this configuration exploits the sensitivity and directionality of this new sensor technology, and overcomes the problem presented by AMR (anisotropic magnetoresistance) sensors that do not have such a strong directional property. FIG. 5 shows the AC characteristics at 50 kHz.

Sensor noise was assessed using a Hewlett Packard HP35665A Dynamic Signal Analyzer. In this experiment, the output was recorded when no magnetic field was applied and the voltage at the bridge input was 5 V. The noise level over a 50 kHz bandwidth was below −120 dB (1 $\mu$V) and the 1/frequency noise could not be observed within the resolution of the measurement.

An experimental benchmark was developed to prove the feasibility of the GMR current probe as an effective flaw detector. Various calibrated defects were machined into the surface of an aluminum plate by using end-milling cutters. The dimensions of the surface defects are as follows:

|  | Length | Width | Depth |
| --- | --- | --- | --- |
| Long crack | 15 mm | 0.5 mm | 2 mm |
| Short crack | 5 mm | 0.5 mm | 2 mm |
| Short crack | 2 mm | 0.5 mm | 1 mm |
| Long edge crack | 12 mm | 0.5 mm | 2 mm |
| Short edge crack | 1 mm | 0.5 mm | 1 mm |
| Circular hole | 5 mm diameter |  | 2 mm |

In addition, an infinitely long crack of varying width was simulated by abutting two plates of aluminum separated by MYLAR™ sheets of constant thickness (0.1 mm). The adjacent surfaces of the two plates were very finely ground to create a good contact in the absence of separating sheets. In this way, a "zero" width crack was simulated.

Figure 6:
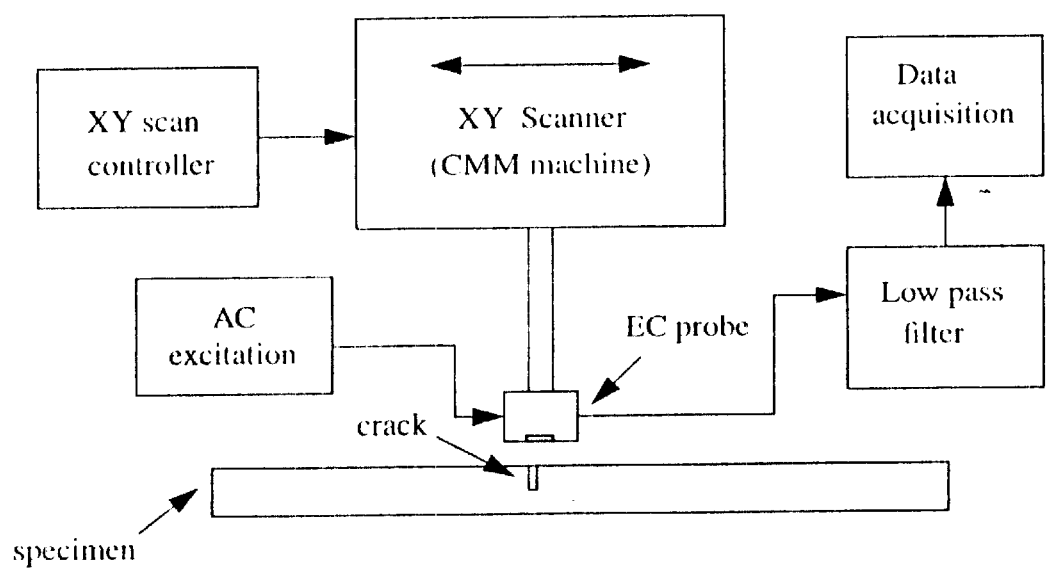
FIG. 6 is a schematic diagram of the experimental setup.

A schematic diagram of the experimental setup is shown in FIG. 6. A sinusoidal current source provided a current through a coil of controlled amplitude (up to 3 A) and frequency (between 1 kHz and 100 kHz). When not specified, the frequency used in the experiments described below was 30 kHz and the amplitude of the current through the coils was 1 A. The GMR ECT probe was scanned over the surface of the specimen in x and y directions by using a CMM (coordinate measuring machine) (Starrett CMM, L.S. Starrett, Athol, Mass.).

A computer program was used to set the scan area and velocity as is known in the art. The CMM can be programmed to scan the specimen over a defined area at a defined scan velocity. This program may also be used to adjust the lift-off distance between the specimen surface and the lower surface of the probe. During measurements, the sensor's output signal was amplified (×20) and filtered by a second order, low pass filter with a cut-off frequency of 10

Hz, using a Stanford Research Systems SR560 Low Noise preamplifier. The input across the two arms of the sensor bridge network was supplied with a DC voltage of 10 V.

A data acquisition program written in LABVIEW™ (standard program, available for example from National Instruments Corp., Austin, Tex.) collected data from the output of the filter via a National Instruments ATMI016X 16 bit analogue to digital converter (National Instruments, Austin, Tex.). For each scanning cycle, samples of filtered signal were collected at a sampling rate specified by the user. Time domain was converted into space domain taking into account the relationship between the number of samples, sampling rate, scanning velocity, and scanning length. The scan in these experiments was a 2D scan in the x-y direction (plane of the specimen). The raster scan mode has been found to be useful, with the data points taken along scans in the x-direction. After a scan in the x-direction along the whole length, the probe is returned to the start position and incremented a short distance (usually 0.3 mm) in the y-direction (no data collected during the y-step). This is repeated until the desired areas has been scanned. The relationship between the scan parameters is give by the equation:

$$L = \frac{vN}{T},$$

where L is the scan distance in the x-direction, N is the number of data points in the x-direction, v is the scan velocity in the x-direction, and T is the interval between two consecutive data points.

Finally, for the visualization of these results, 3-D maps representing the output voltage of the sensor (amplified and filtered) as a function of x-y displacement were plotted.

The probe used to produce the results shown in FIGS. 7–14comprised a cylindrical coil of 5 mm radius. In the example herein, first the probe was scanned over the 15 mm long crack with the orientation of the sensitive axis of the sensor perpendicular to the direction of the crack. The map obtained from these experiments, shown in FIG. 7(a), shows two symmetrical peaks that are located on each side of the crack. Beside the central maxima at either side of the crack, each peak has two shoulders, and the distance between the shoulders coincides with the length of the crack. This can be more clearly seen in FIG. 7(c) which shows the x-axis displacement. From FIG. 7(b), the position of the crack in the y direction can be precisely located mid-way between the two symmetrical peaks. Therefore, this map contains enough information to determine both the location and the length of the crack (defect reconstruction).

Figure 8A:
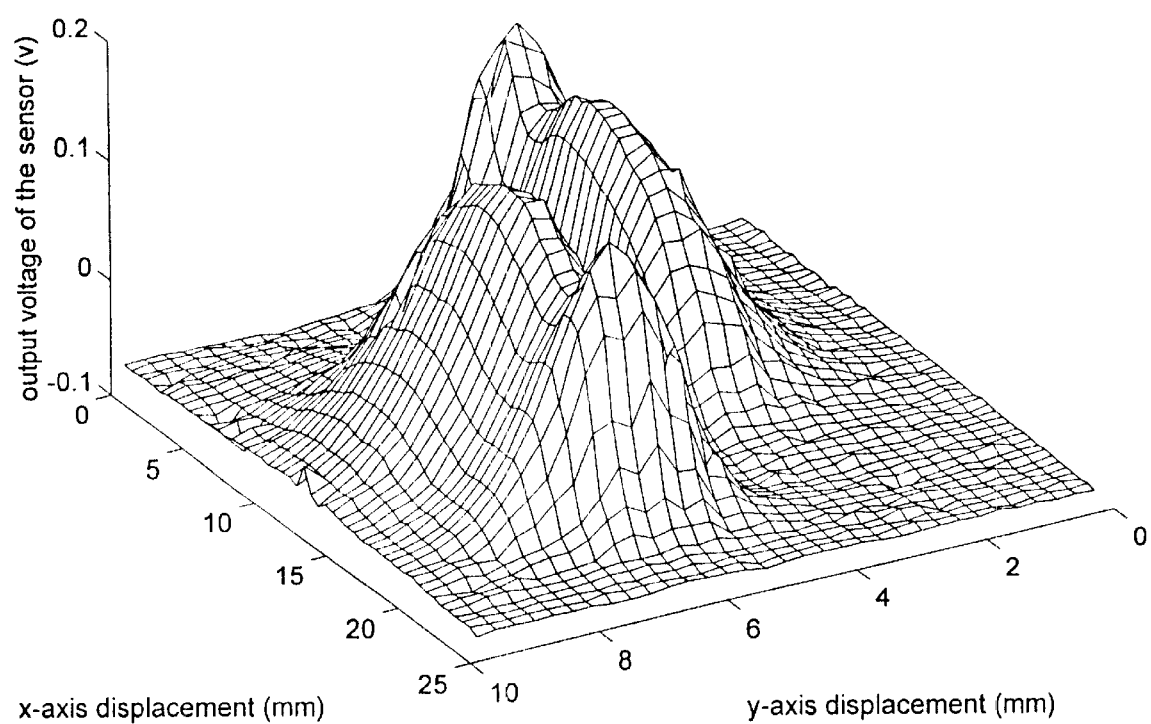
FIG. 8(a) is a two-dimensional map of the crack shown in FIG. 7(a) after rotation of the sensitive axis.

Rotating the sensitive axis by 90 degrees, the central regions of both peaks on either side of the crack both decrease in magnitude, while the amplitude of the shoulders varies as shown in FIG. 8(a). In particular, for each pair of shoulders, one shoulder decreases in magnitude, while the other increases in magnitude. Simultaneously, as the sensitive axis is rotated, the position of the high shoulders, which become peaks, moves in an arc about the crack tip. Finally, with the sensitive axis oriented along the crack (FIG. 8(b)), only two peaks remain, with a line drawn between the two being coincident with the line of the crack. The distance between these two peaks is longer than the actual length of the crack.

Figure 7A:
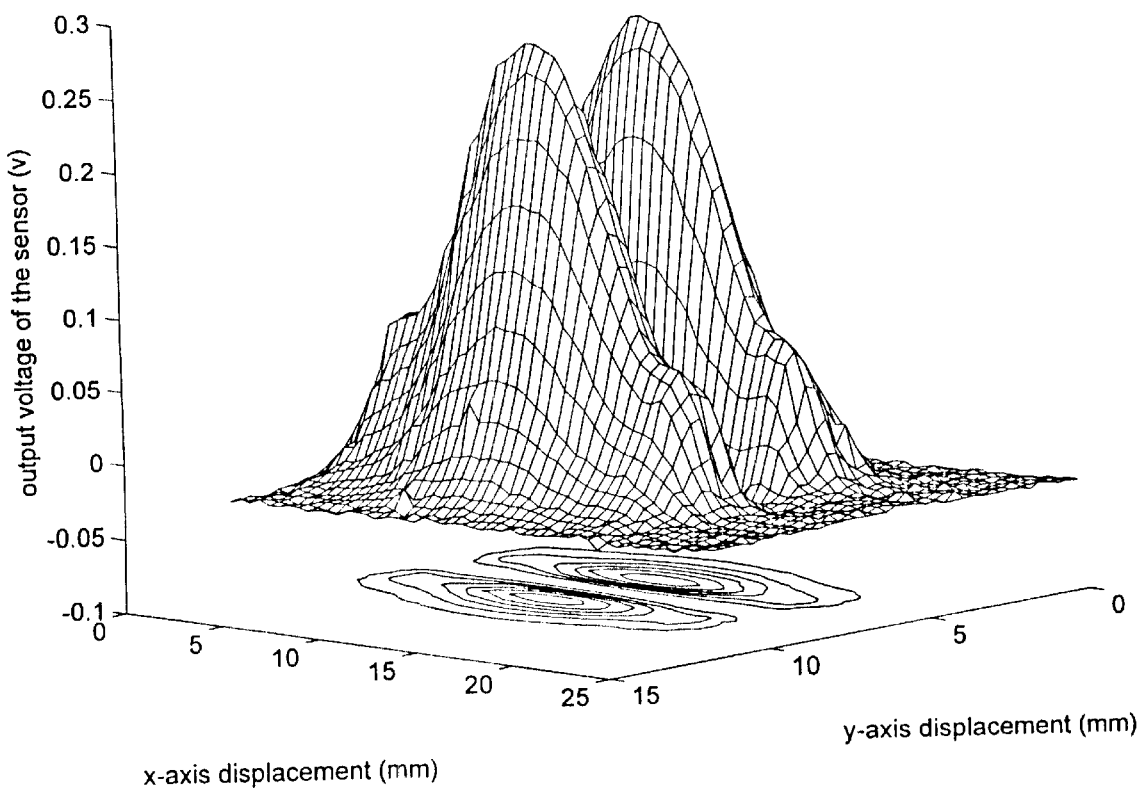
FIG. 7(a) is a two-dimensional map showing the magnitude and contours of sensor output after scanning a crack of length 15 mm with the sensitive axis perpendicular to the crack orientation.
Figure 7B:
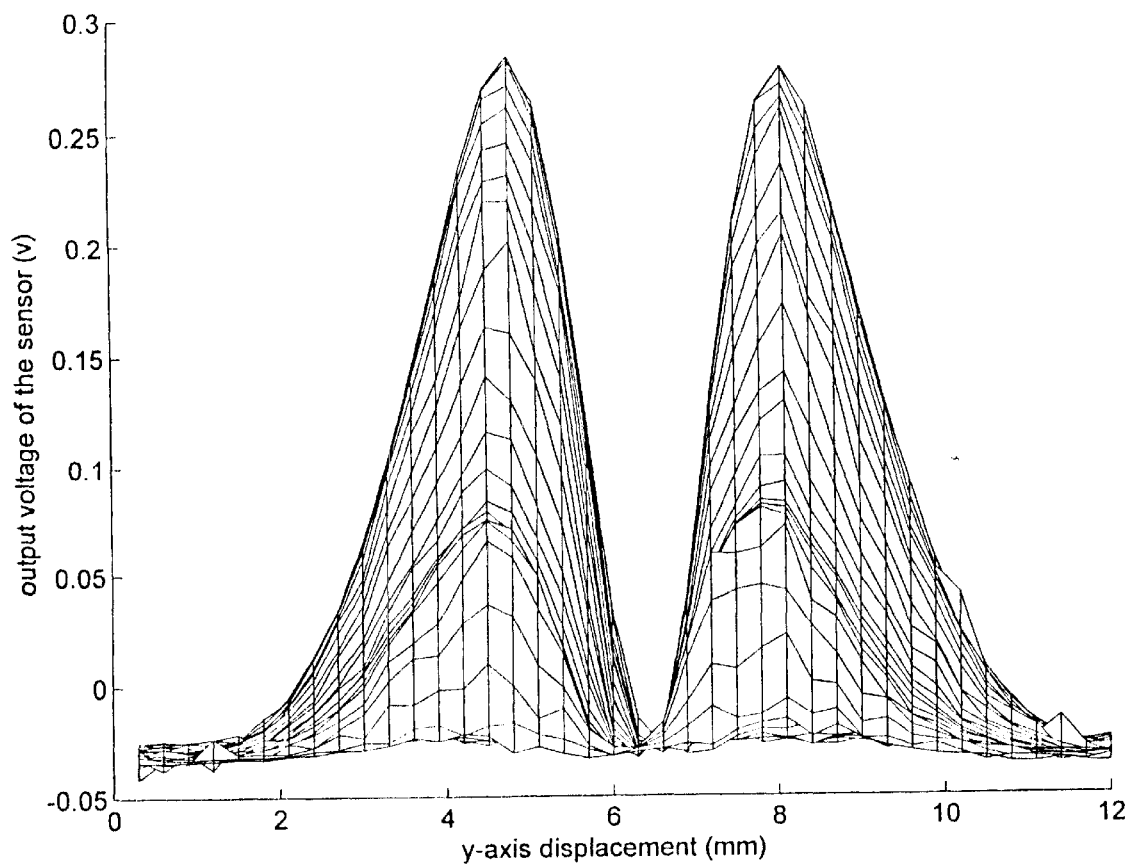
FIG. 7(b) is a graph showing y-axis displacement in mm of the scan shown in FIG. 7(a).
Figure 7C:
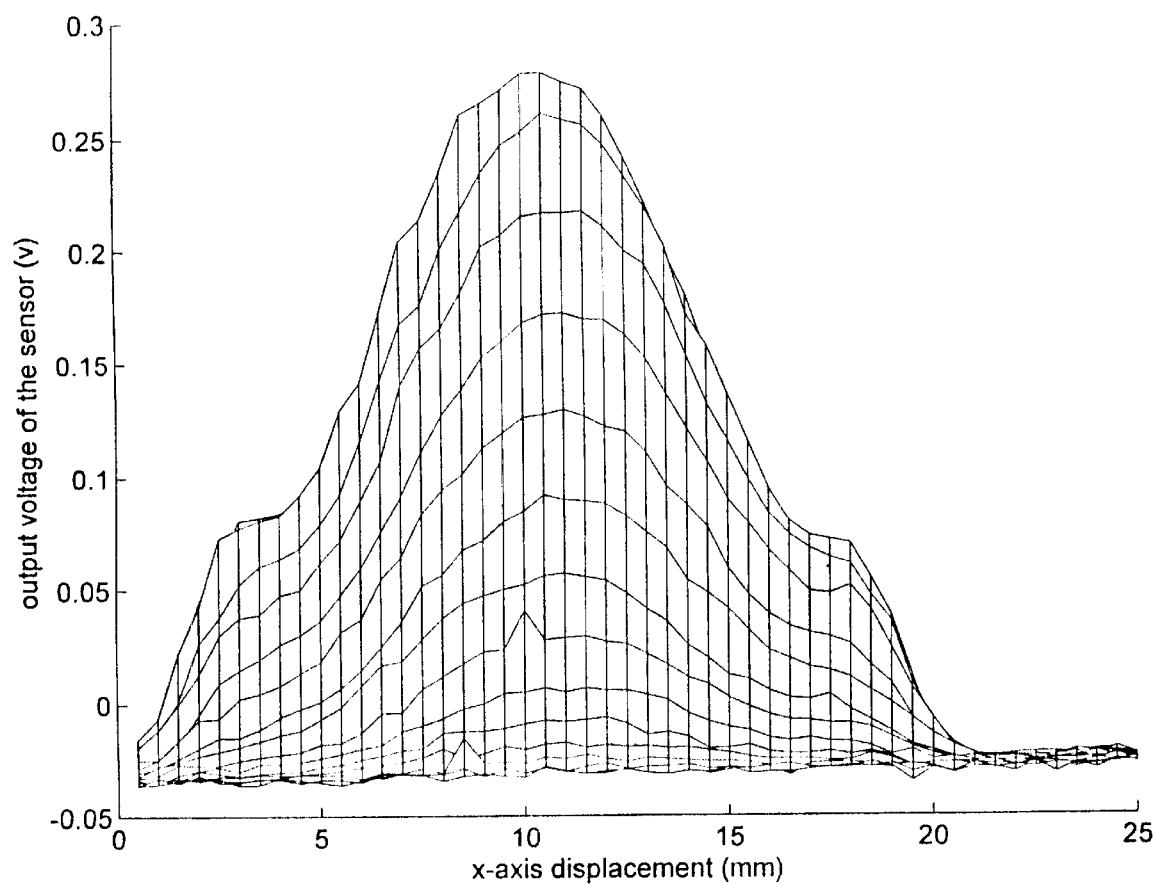
FIG. 7(c) is a graph showing x-axis displacement in mm of the scan shown in FIG. 7(a).
Figure 8B:
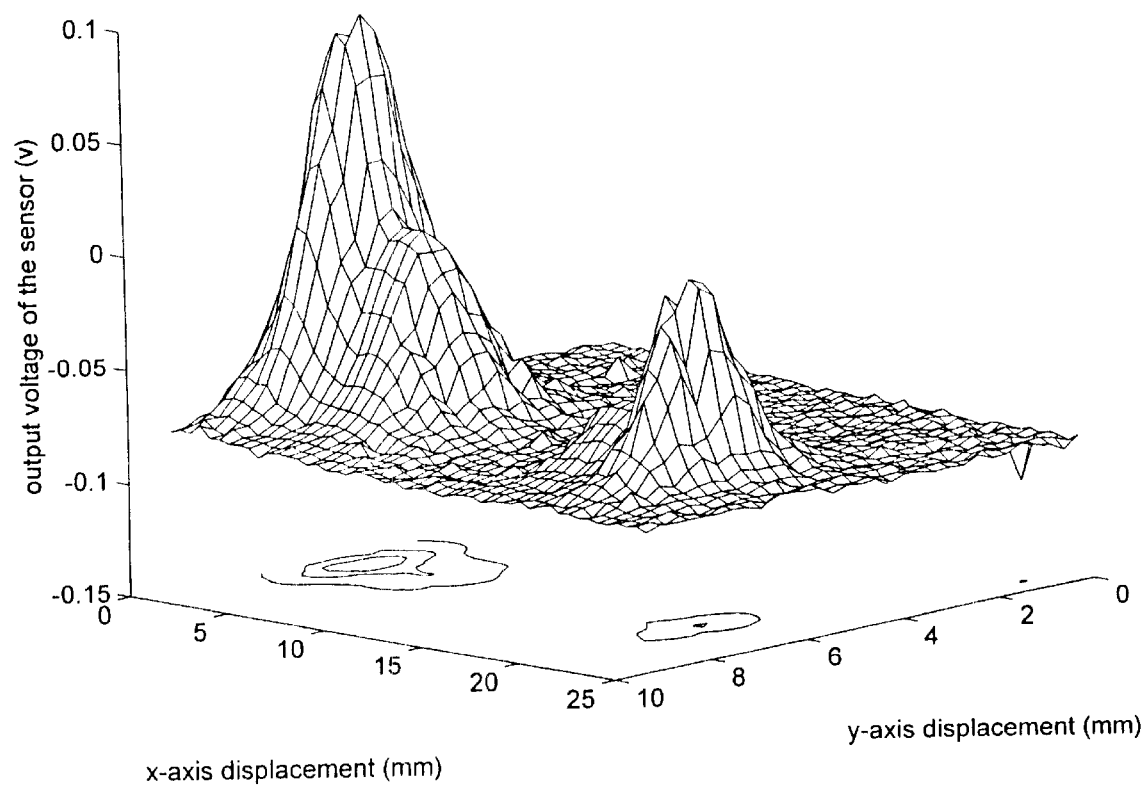
FIG. 8(b) is a two-dimensional map of the crack shown in FIG. 7(a) with the sensitive axis oriented along the crack.
Figure 9:
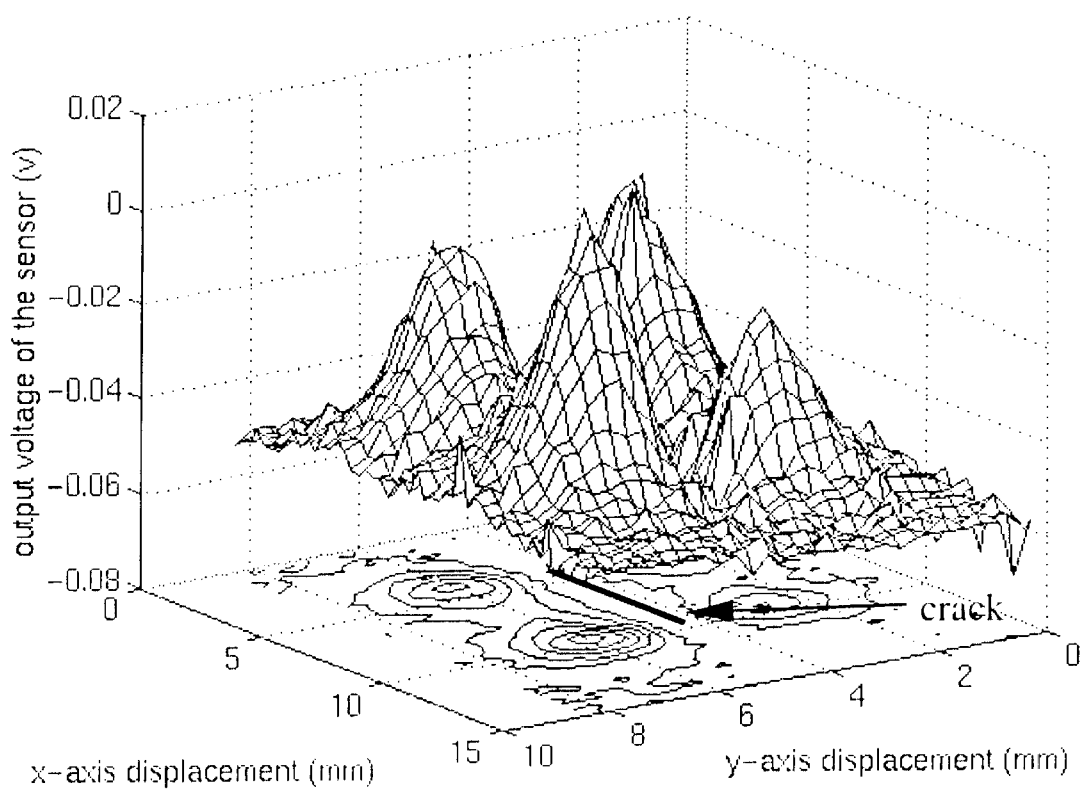
FIG. 9 is a two-dimensional map showing the magnitude and contours of sensor output after scanning a crack of length 5 mm with the sensitive axis perpendicular to the crack.

Being shorter than the diameter of the coil, the 5-mm long crack was scanned by the probe with the sensitive axis perpendicular to the crack. The result is shown in FIG. 9. In this case, what had been the shoulders for the long crack as shown in FIG. 7(a) became pairs of peaks on either side of the crack at the ends of the crack on each side of it. The asymmetry in FIG. 8(b) and FIG. 9 are due to misalignment between the probe and the specimen's surface during measurement.

Figure 10:
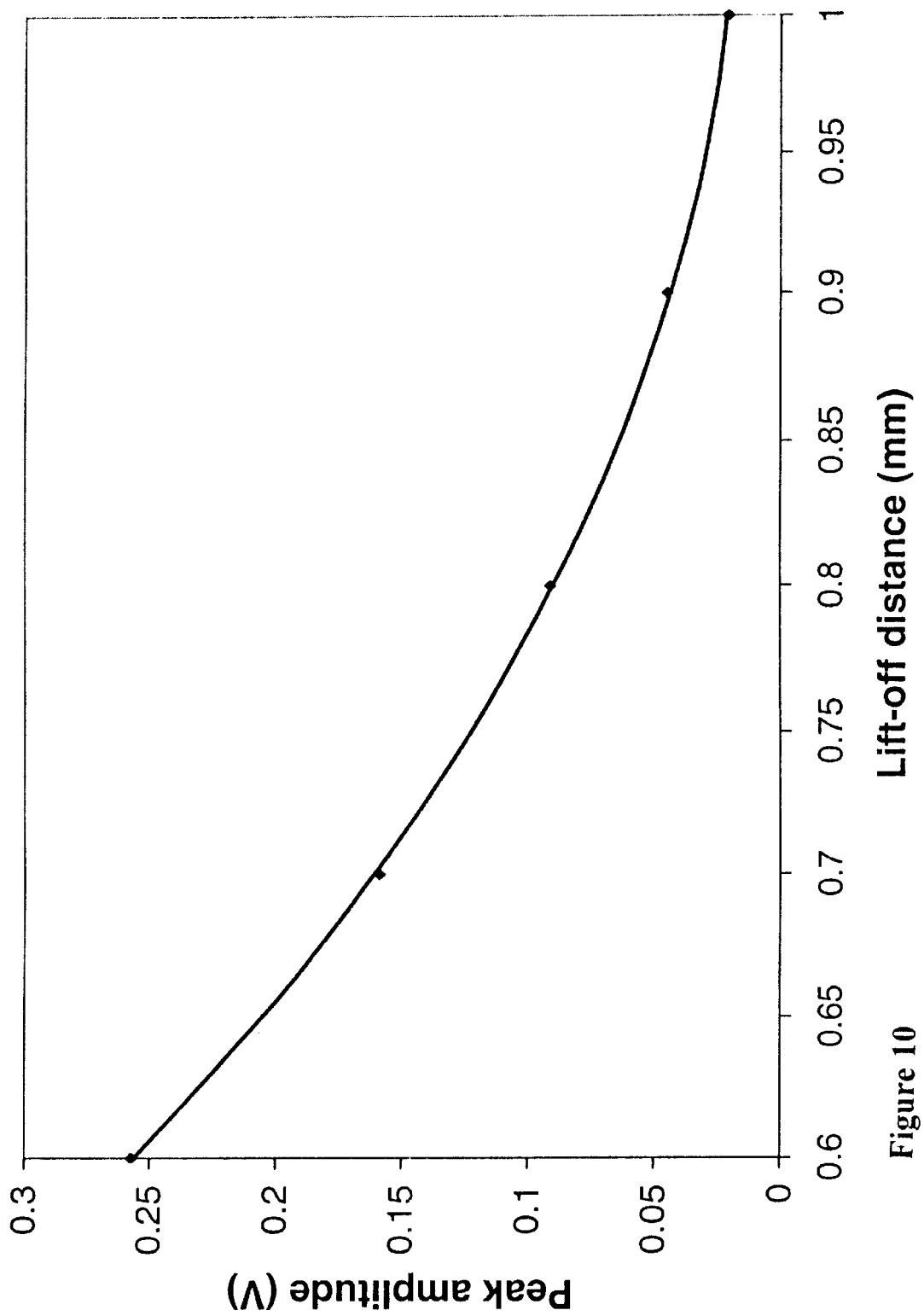
FIG. 10 shows the decrease of the amplitude of the symmetrical peaks on either side of the crack when the lift-off distance is increased.

To study the influence of the separation between the lower surface of the probe and the upper surface of the specimen (the "lift-off distance"), the 15 mm long crack was scanned while the lift-off distance was varied between 0.6 mm and 1 mm, at 0.1 mm increments, with the sensitive axis perpendicular to crack orientation. The shape of the maps obtained is similar to the map shown in FIG. 7(a), but the amplitude of the symmetrical peaks on either side of the crack decreased as the lift-off distance increased. This dependence is shown in FIG. 10, with the amplitude decreasing in an approximately exponential manner. It was observed that the distance between the two shoulders in the x direction (FIG. 7(c)) is constant and does not depend on the lift-off distance. Therefore, the lift-off is not critical for determination of crack length.

Figure 11:
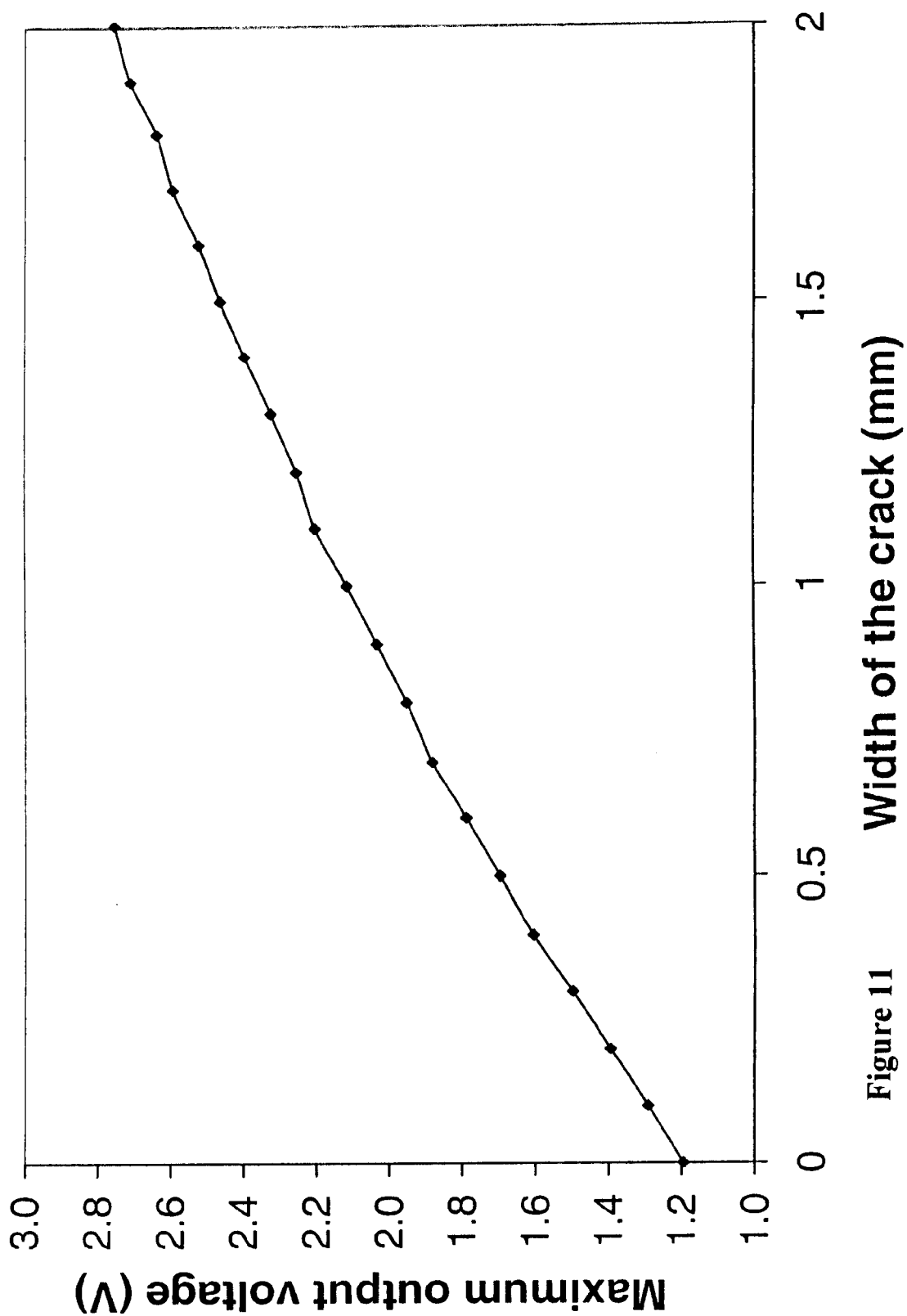
FIG. 11 shows the amplitudes of the peak as a function of crack width.

The effect of crack width on the output of the sensor was studies using two precisely machined plates with ground edges that were placed adjacent each other to form a long crack. First, measurements were performed wit the two plates in contact. Ignoring the effects of surface finish and other manufacturing tolerances, this was considered to approximate an infinite crack with zero separation between the two surfaces. Subsequently, inserting MYLAR™ sheets (thickness of 0.1 mm each) between the plates varied the crack width. During the experiments, the lift-off distance remained constant and the sensitive axis was perpendicular to the crack direction. The amplitudes of the peak as a function of crack width is shown in FIG. 11. The results show that the output voltage increases, slowly tending toward a maximum value of around 3 V, for rather unrealistic crack widths of over 2 mm. Further enlarging this width, it was observed that saturation of the peak value occurs at around 10 mm separation, and primarily depends on the coil diameter. For separations of greater than 10 mm, the sensor measures the edge influence of only one plate (half-crack). The most striking result is that there is a large output signal even when the plates are in electrical contact. This can be explained by the large resistivity of the contact in comparison to the bulk of the plate, which produces almost the same deviation of the eddy current paths as for a crack of finite width. The large contact resistivity is probably due to the oxide deposited on the edges and imperfectly polished surfaces.

The influence of the amplitude of the excitation current in the coil was also assessed. In these measurements, the 15 mm crack was scanned with the sensitive axis perpendicular to the crack orientation. An approximately linear increase of the peak amplitude with excitation current was obtained. The distance between the shoulders, as discussed with respect to FIG. 7(c), was constant and does not depend on the excitation current; therefore reconstruction of cracks can be carried out at any excitation amplitude. These results are consistent with the equation for calculation of radial current density as a function of known fact that detected field is proportional to eddy current density.

Figure 12:
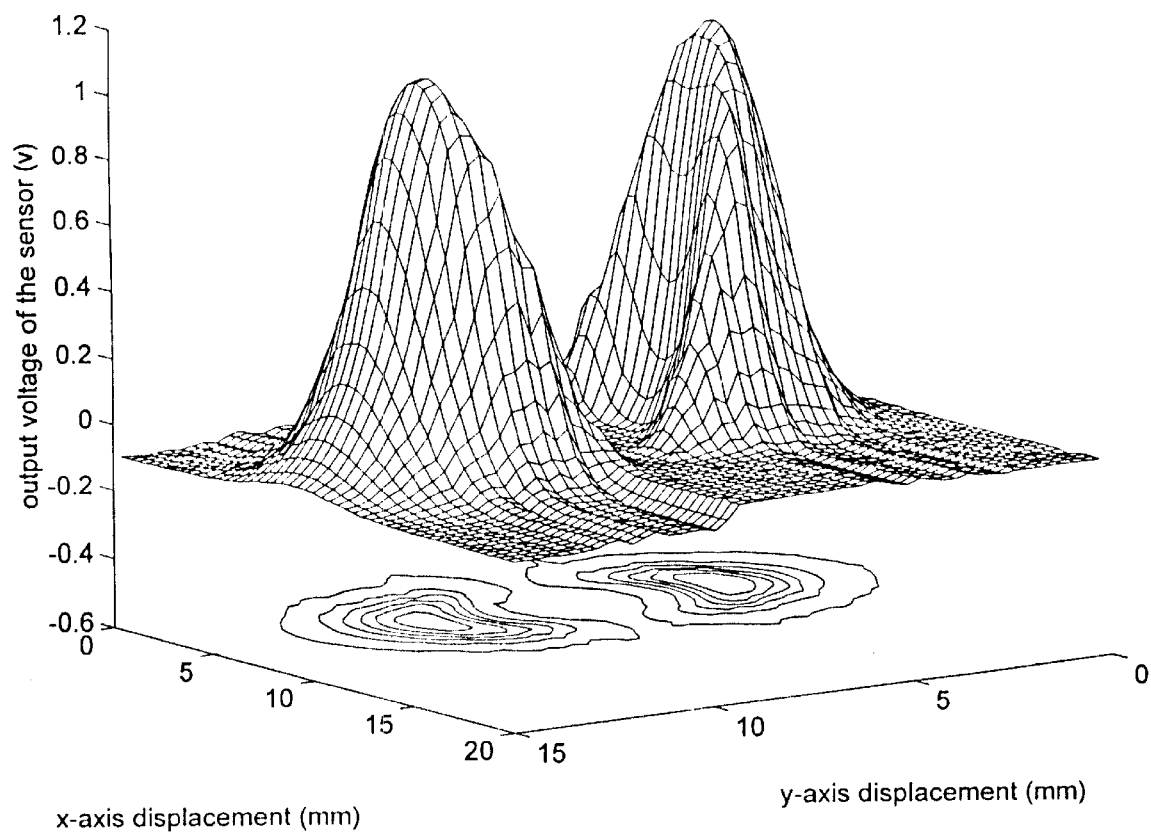
FIG. 12 shows the 3-D map obtained after scanning a 5 mm diameter, 2 mm deep drilled hole with the sensitive axis oriented in the y direction.

In addition to cracks, the device of the invention can be used to measure other defects. FIG. 12 shows the 3-D map after scanning a 5 mm diameter, 2 mm deep drilled hole with the sensitive axis oriented in the y direction. The shape of the field contours obtained shows that the circular shape can be reconstructed, and the center of the hole can be located.

A difficult problem in eddy current inspection of parts is the detection of cracks near sharp edges. Since the edge is a geometric discontinuity, it produces a strong eddy current response that can distort the crack signal, resulting in a degradation of the capability to reliably detect the crack. The GMR based probe of the invention herein provides a simple solution to this problem. When the probe is scanned above a crack initiating perpendicular to the edge, orienting the sensing axis parallel to the edge, the output signal is produced only by the crack, while the usually high signal due to the edge is eliminated.

Figure 13:
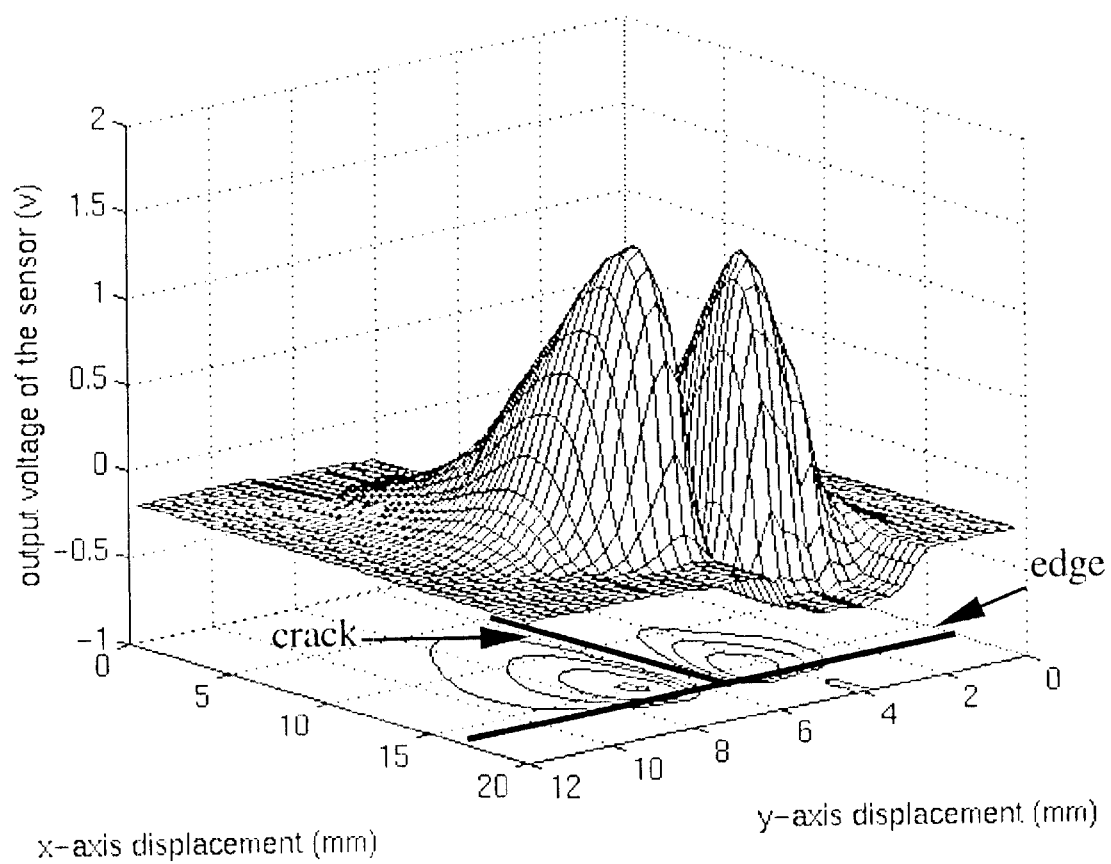
FIG. 13 shows the output after scanning an edge crack 12 mm in length with the sensing axis perpendicular to the crack (parallel to the edge).

FIG. 13 shows the output sensor when scanning a surface crack initiating on an edge of an aluminum specimen, oriented perpendicular to this edge. During the scan, the sensing axis was parallel to the edge. In this map, the edge has no effect on the sensor's output. It is noted that the signal of the sensor produced by the crack has similar shape to the signal in FIG. 7(a). The only difference is that the peaks on each side of the crack are not symmetrical. As in FIG. 7(a), the position of the crack is midway between the two peaks. Moreover it can be noticed that the magnitude of the peaks (1.5 V) is much higher in the case of the edge crack than it is for an inside crack of the same dimensions. This implies that the presence of the edge enhances the sensitivity of the measurement.

Figure 14:
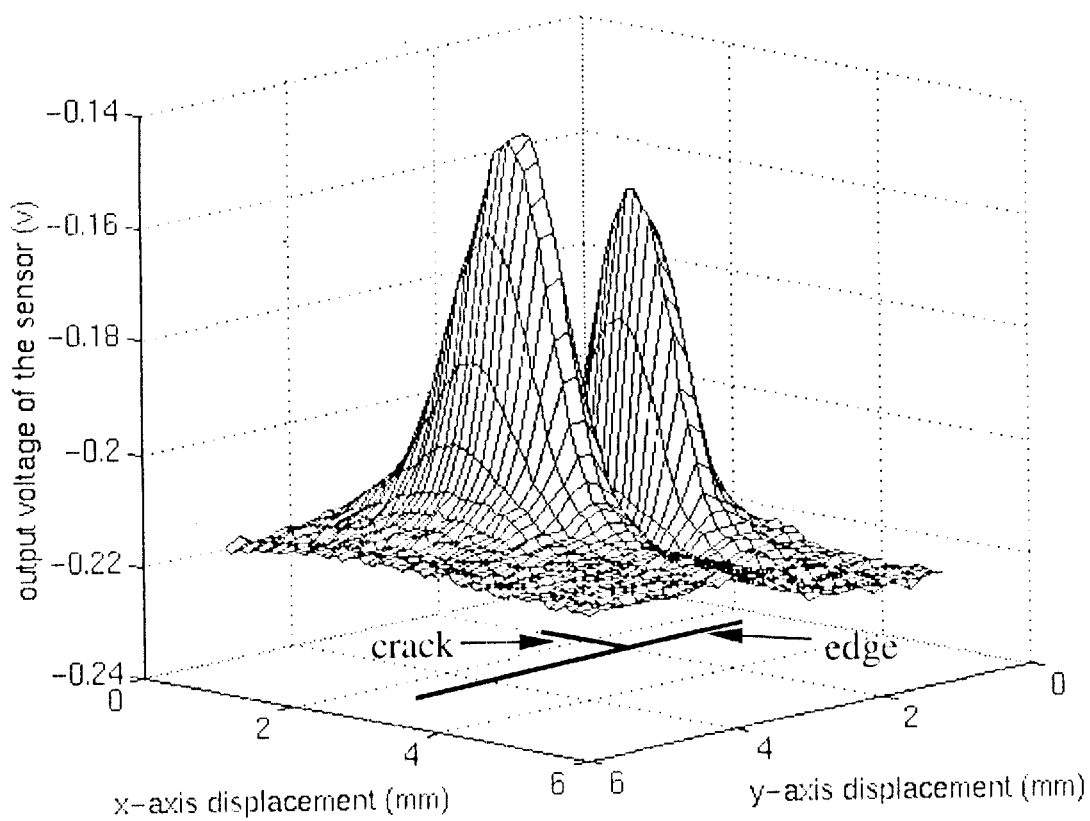
FIG. 14 shows the output after scanning an edge crack 1 mm in length with the sensing axis perpendicular to the crack (parallel to the edge).

The map obtained by scanning an edge crack of 1 mm length, 0.5 mm width and 1 mm depth is shown in FIG. 14. The peak amplitude is about 50 mV. It can be noticed that this crack can be reliably detected even though its main dimension is much smaller than the mean diameter of the coil (10 mm). Detection of such a defect using the same probe was not possible in the case of a crack of similar dimensions occurring on the surface far from an edge.

Figure 15A:
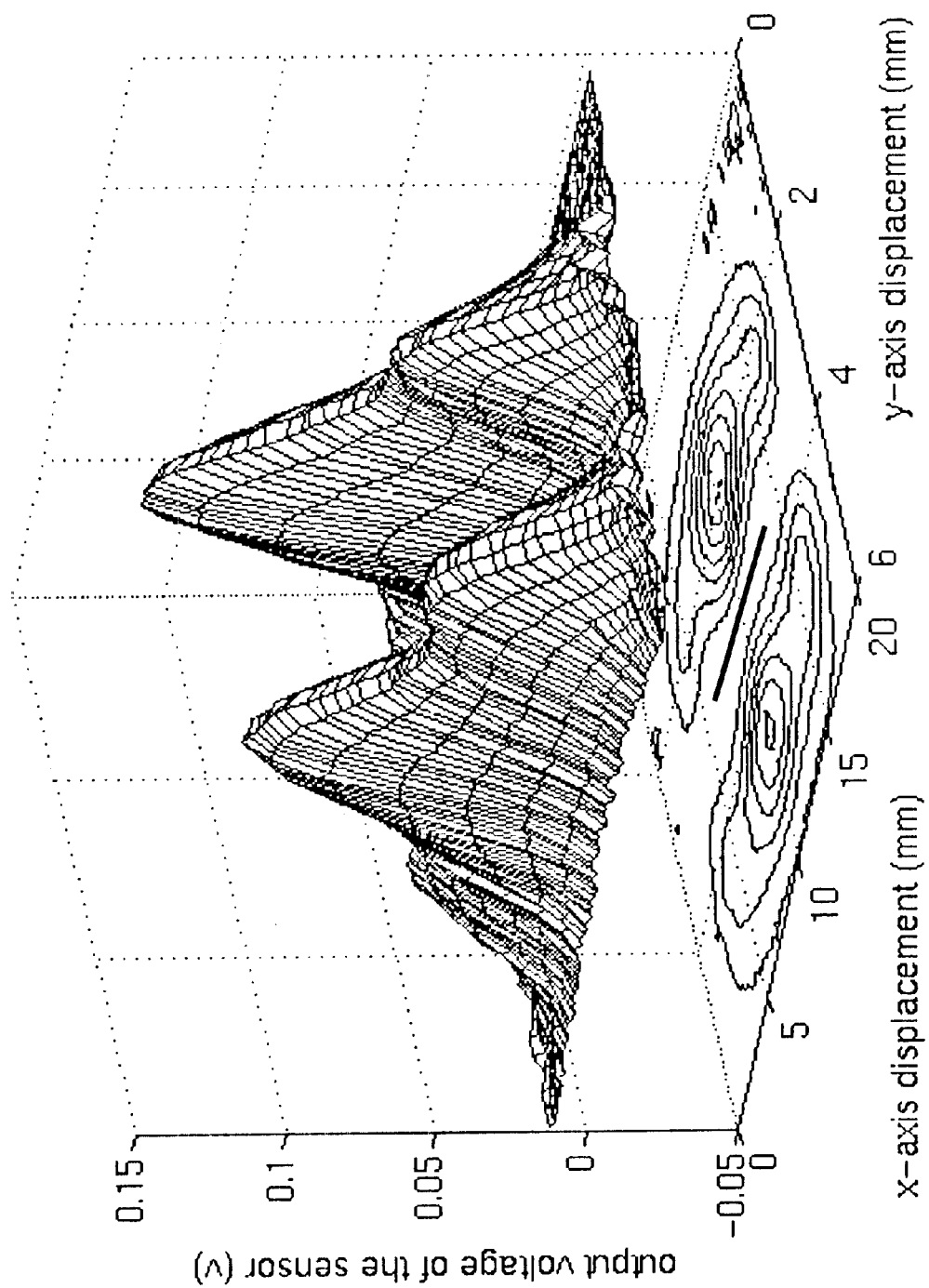
FIG. 15(a) shows the output after scanning a crack 5 mm in length using a flat coil of mean radius 1.8 mm, with the sensing axis perpendicular to the crack.
Figure 15B:
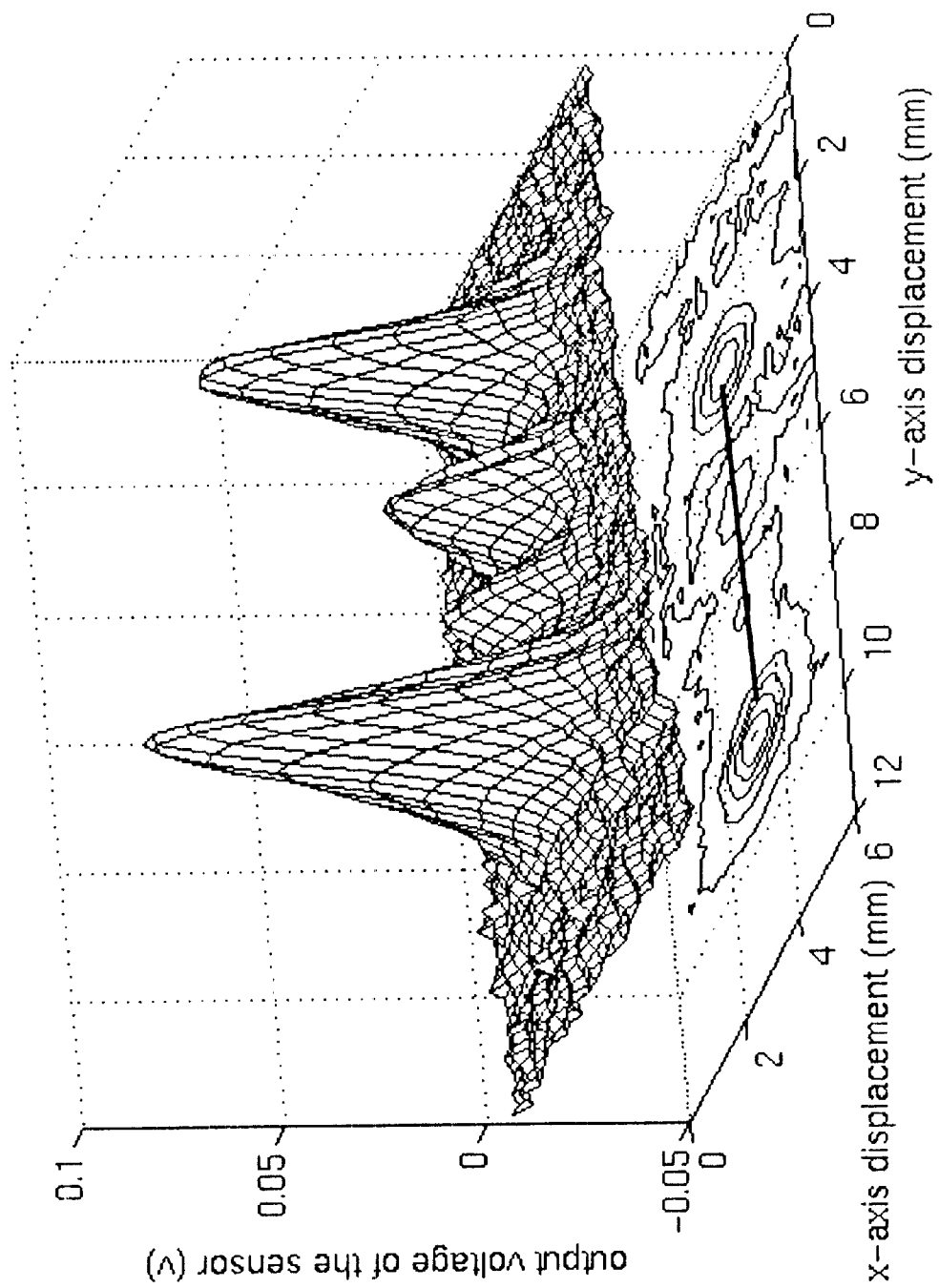
FIG. 15(b) shows the output after scanning a crack 5 mm in length using a flat coil of mean radius 1.8 mm, with the sensing axis parallel to the crack.

A flat coil probe design, the mean radius of the coil being 1.8 mm, has been used in the following experiments. The result of scanning the 5 mm long crack is shown in FIG. 15(a). The sensing axis was perpendicular to the crack direction. As it can be observed, the map is similar to that of FIG. 7(a). This demonstrates that the crack of 5 mm length is "short" relative the large coil (5 mm radius, see FIG. 9) and the same time is "long" relative to the small flat coil (1.8 mm radius, see FIG. 15(a)). The map obtained from the flat coil probe with the sensing axis parallel to the crack orientation is shown in FIG. 15(b). In this map, it can be observed that there are two pairs of peaks corresponding to the tips of the crack.

Figure 16:
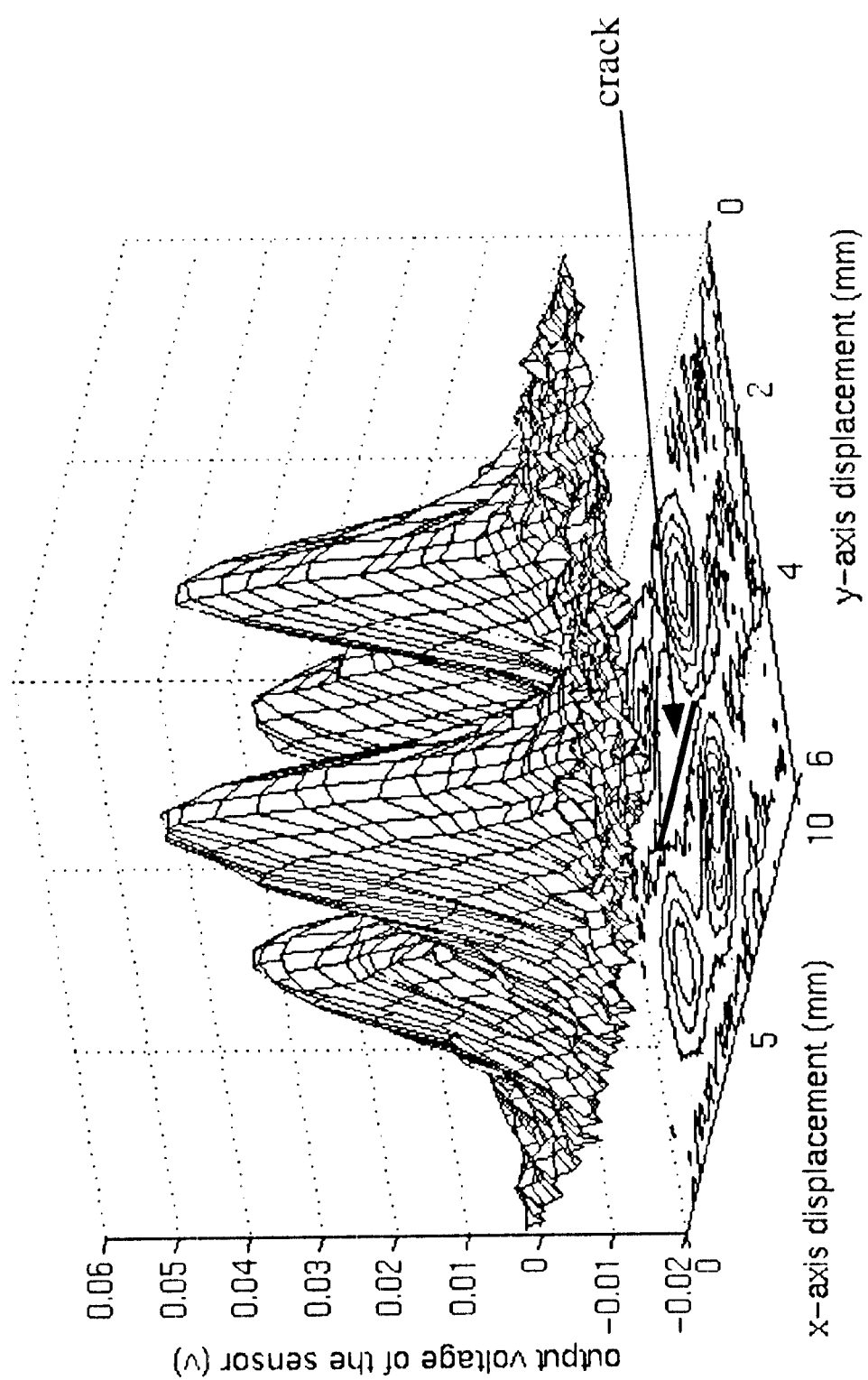
FIG. 16 shows the output after scanning a crack 2 mm in length using a flat coil of mean radius 1.8 mm, with the sensing axis perpendicular to the crack.

To demonstrate that reducing the coil diameter leads to an improved spatial resolution of crack detection, a short crack of 2 mm length was canned using the same flat coil probe. The sensing axis was perpendicular to the crack direction. The map obtained from this scan is shown in FIG. 16. It can be noted that the map is similar to that shown in FIG. 9. The same crack (2 mm long) could not be detected using the large coil (5 mm radius). It is expected that correspondingly shorter cracks can be detected by further reducing the coil diameter.

The directionality of the probe of the invention provides additional information to enhance the unambiguous deconvolution for the assessment of crack dimensions and location.

The magnitude of the detected field can be estimated from the experimental results. Knowing the AC sensitivity S of the sensor (S=220 mV mT$^{-1}$ for 10 V bridge supply) and amplification of the filter A$_v$=20, the rms value of the detected field can be computed from:

$$B_{det} = \frac{V_{out}}{S\,A_v}$$

where V$_{out}$ is the filtered output voltage of the sensor.

The peak amplitude of the output when scanning a 15 mm long crack is approximately 0.3 V (from FIG. 7(a)), giving B$_{det}$=68.2 μT.

The maximum output voltage recorded during the experiments was 3.7 V corresponding to an infinitely long, 10 mm wide crack, which is effectively an edge. This voltage corresponds to B$_{det}$=840 μT.

The GMR eddy current probe of the invention allows the location of defects and evaluation of crack length. In addition, due to its reduced dimensions, the sensor gives the local map of the distribution of the tangential (to the specimen surface) component of the magnetic field resulting from the interaction between crack and magnetic field produced by the coil. This map can be verified by using numerical methods, for example, the finite element method known in the art.

The signal conditioning circuit of the GMR sensor of the invention is very simple, comprising only a differential amplifier and a low pass filter. Because of the planar technology of GMR sensors, the signal conditioning circuit can be integrated on the same chip with the sensor bridge. Besides the reduced area, the integration provides an improved signal/noise ratio.

The dimensions of the coil limit the spatial resolution of the probe. The minimum crack length that can be detected is roughly equal to the coil mean radius. Considering the dimension of the GMR sensor of the invention as used in the experimental example above, reducing the scale of the probe design presents no immediate technological challenges.

The GMR sensor is extremely sensitive, being able to detect magnetic fields of the order of 10$^{-5}$ T, and that in the types of studies discussed above, the GMR sensor operates in the linear region (maximum B$_{det}$ was 840 μT) and does not saturate (B$_{sat}$ is 2 mT). The sensitivity and saturation field of the sensor can be customized by choosing a proper structure of the GMR multi-layer.

The GMR sensor of the invention can be integrated with other planar manufactured circuits, such as are set forth in U.S. Pat. No. 5,617,071.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. An eddy current sensor, comprising:
   a) a giant magnetoresistive sensor having a sensing plane and a sensing direction within said sensing plane; and
   b) a rotationally symmetric flat pancake-type coil having an axis of symmetry, wherein said giant magnetoresistive sensor is centered at the axis of symmetry of the coil, with the sensing plane and sensing direction being perpendicular to the axis of symmetry of the coil, and wherein said coil is placed between the giant magnetoresistive sensor and a specimen.

2. The eddy current sensor according to claim 1, having a number of layers that is a multiple of two.

3. The eddy current sensor according to claim 1, wherein the pancake type coil and the giant magnetoresistive sensor are deposited on the same substrate.

4. The eddy current sensor according to claim 3, wherein the substrate is silicon.

5. The eddy current sensor according to claim 1, wherein the eddy current sensor further comprises a signal conditioning circuit comprising a differential amplifier and a low pass filter.

6. The eddy current sensor according to claim 1, wherein the giant magnetoresistive sensor is self-rectifying, to simplify signal conditioning circuitry.

7. The eddy current sensor according to claim 1, wherein the sensor has a broad bandwidth enabling a large range of excitation frequencies, in turn enabling variation of skin depth on the surface for measurement of defects of varying depth or of sub-surface defects.

8. The eddy current sensor according to claim 1, wherein the eddy current sensor is produced in a configuration so that the component of the magnetic field in the direction of the sensitive plane, parallel to the surface of the specimen, can be measured.

9. A method for detecting anomalies such as cracks at the edge of a specimen, comprising:
  a) providing an eddy current probe comprising a giant magnetoresistive sensor having a sensing plane and a sensing direction within said sensing plane, and a rotationally symmetric coil having an axis of symmetry, wherein said giant magnetoresistive sensor is centered at the axis of symmetry of the coil, with the sensing plane and sensing direction perpendicular to the axis of symmetry of the coil;
  b) orienting the sensitive plane of the giant magnetoresistive sensor parallel to the specimen surface;
  c) orienting the sensing direction of the sensor parallel to said edge of the specimen, so that the output signal is insensitive to said edge, but so that perturbations of eddy currents due to the presence of cracks at said edge are monitored by the probe;
  d) passing an alternating current through the coil placed adjacent to the specimen surface, said coil placed with its axis of symmetry perpendicular to the specimen surface, to induce circulating currents in the specimen surface plane; and
  e) utilizing said probe to scan the surface in a region including said edge to produce an output signal that enables detection of said anomalies.

10. The method according to claim 9, wherein the coil is a flat pancake type coil located between the giant magnetoresistive sensor and the specimen surface.

11. The method according to claim 10, wherein the pancake type coil and the giant magnetoresistive sensor are deposited on the same substrate.

12. The method according to claim 9, wherein the eddy current sensor comprises a signal conditioning circuit comprising a differential amplifier and a low pass filter.

13. The method according to claim 9, wherein the sensor has a broad bandwidth enabling a large range of excitation frequencies, in turn enabling variation of skin depth on the surface for measurement of defects of varying depth or of sub-surface defects.

14. The method according to claim 9, wherein the eddy current sensor is produced in a configuration so that the component of the magnetic field in the direction of the sensitive axis, parallel to the surface of the specimen, can be measured.

15. An apparatus comprising the eddy current sensor according to claim 4, a signal conditioning circuit comprising a differential amplifier and a low pass filter, wherein at least some of the apparatus is integrated on the silicon substrate.

16. The method according to claim 9, wherein the coil is a circular cylinder surrounding the giant magnetoresistive sensor, and wherein the giant magnetoresistive sensor is placed as near to the specimen surface as is practical.

17. A method for detecting anomalies and features such as cracks in a specimen surface, comprising:
  a) providing an eddy current sensor according to claim 1;
  b) orienting the sensitive plane of the giant magnetoresistive sensor parallel to the specimen surface;
  c) passing an alternating current through the coil placed adjacent to the specimen surface, said coil placed with its axis of symmetry perpendicular to the surface, to induce circulating currents in the specimen surface plane; and
  d) utilizing said probe to scan the surface to produce an output signal that enables detection of said anomalies and features.

18. A method according to claim 17, further comprising determining the location and length of a detected crack by orienting the sensitive direction of the sensor perpendicular to the crack.

19. The method according to claim 17, wherein the coil and the giant magnetoresistive sensor are deposited on the same substrate.

* * * * *